(12) United States Patent
Nislow et al.

(10) Patent No.: US 6,743,897 B1
(45) Date of Patent: Jun. 1, 2004

(54) ASPERGILLUS FUMIGATUS PROFILIN

(75) Inventors: Corey E. Nislow, San Francisco, CA (US); Kee Wong, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/724,512

(22) Filed: Nov. 27, 2000

(51) Int. Cl.[7] .................. C07K 16/00; A61K 38/00; C12N 1/00; C12N 1/14
(52) U.S. Cl. .................. 530/388.5; 530/300; 530/324; 530/388.2; 530/388.26; 435/243; 435/254.1; 435/254.3; 435/256.1
(58) Field of Search .................. 435/325, 324, 435/341; 530/300, 371, 388.5

(56) References Cited

U.S. PATENT DOCUMENTS

| | | |
|---|---|---|
| 6,111,072 A | 8/2000 | Narumiya et al. |
| 6,171,798 B1 | 1/2001 | Levine et al. |
| 6,197,932 B1 | 3/2001 | King et al. |

FOREIGN PATENT DOCUMENTS

| | | |
|---|---|---|
| WO | 97/31104 | 8/1997 |
| WO | WO 97/31104 * | 8/1997 |
| WO | WO 00/39287 A2 | 7/2000 |
| WO | 00/61598 | 10/2000 |

OTHER PUBLICATIONS

Haarar et al, The Journal of Cell Biology, vol. 110, Jan. 1990.*

Oechsner et al, Nucleic Acids Research, vol. 15, No. 21, 1987.*

Pollard et al, Biochemistry, vol. 23, 1984, p. 6631–6641.*

Thomas E. Creighton, in his book, "Proteins: Structures and Molecular Properties, 1984", pp. 314–315.*

Thomas E. Creighton, in his book "Protein Structure: A Practical Approach, 1989"; pp. 184–186.*

Thomas E. Creighton, in his book, Proteins: Structures and Molecular Properties, 1984.*

Nosoh, Y. et al in "Protein Stability and Stabilization through Protein Engineering, 1991" (chapter 7, p. 197, second paragraph).*

Tsang et al., "*Aspergillus niger* Expressed Sequence Tags," Database EMBL Online! EBI, Sep. 20, 2000, Database accession No. BE759614, XP002216292, abstract only.

Balasubramanian et al., "The Schizosaccharomyces pombe cdc3+ gene encodes a profiling essential for cytokinesis," Database SWALL Online! EBI, Feb. 1, 1995, Database accession No. P39825, XP002216284.

* cited by examiner

Primary Examiner—Lynette R. F. Smith
Assistant Examiner—Vanessa L. Ford
(74) Attorney, Agent, or Firm—Lauren L. Stevens; Townsend and Townsend and Crew LLP

(57) ABSTRACT

The invention provides isolated nucleic acid and amino acid sequences of *A. fumigatus* profilin, methods of screening for *A. fumigatus* profilin modulators using biologically active *A. fumigatus* profilin, and kits for screening for *A. fumigatus* profilin modulators.

4 Claims, 3 Drawing Sheets

FIG. 1

```
ATGGGTCAGC ACTCGGCAGT TTGGCAAGGA TATGTTGATT CCAGTTTGAT
GGGCTCCGGC CAGTTTGACA AGGCCGCCAT TCTGAGCTAC GACTTCTCCG
ACGTCGAGGC CCAGTCCCCT ACTTTCCAGA TCTCGAAGGA GGAAATTGCC
GGGCTGAAGG CTGCTTTCGA CAAGCCTGGC AGTGCTTTCG AAACCGGTTT
CGTGGTCGGA GGAGACAAGT TCGTCGCCAT CAAGGCTGAT GATCGCAGTC
TCTACGGCAA GAAGGGCAAA GAGGGTATCG TCGTCGTCAA GGCCGTCTCT
TGCGTCATGG TGGCCCATCA TGGCGAGGCC GTTCAGACCA CCAACGCTGC
AACCGTTGTC GAGAACCTCG TCGACTACAT CAACAACCCC CGGTAG
```

ASPERGILLUS FUMIGATUS PROFILIN

FIELD OF THE INVENTION

The present invention relates to a gene involved in actin dynamics and phospholipid hydrolysis in the yeast *Aspergillus fumigatus* and more particularly to the identification, isolation and cloning of this gene. This invention also relates to a method of using this gene to screen for compounds with antifungal activity.

BACKGROUND OF THE INVENTION

Profilin is a ubiquitous 12–15 kDa eukaryotic actin and phosphotidylinositol-4,-5-biophosphate-($PIP_2$) binding protein. Machesky and Pollard (1993) Trends Cell Biol. 3:381–5. In mammalian cells, the protein functions by binding $PIP_2$ which inhibits the phospholipid hydrolysis by phospholipase C (PLC) in resting cells. Goldsmidt-Clermont et al. (1990) Science 247:1575–8. When cells divide following activation of tyrosine kinase receptors, PLC is phosphorylated and thereby activated to hydrolyze $PIP_2$ even in the presence of profilin. Goldschmidt-Clermont et al. (1991) Science 251:1231–3. This hydrolysis releases the known messengers inositol triphosphate ($IP_3$) and diacylglycerol (DAG) and profilin. Profilin moves from the plasma membrane to the cytosol, where it binds to actin to catalyze the rearrangment of the cytoskeleton. Goldschmidt-Clermont and Jamey (1991) Cell 66:419–21.

Profilin catalyzes release of adenosine diphosphate (ADP) from monomeric or globular (G-) actin. Mockrin et al. (1980) Biochem. 19:5359–62; Goldschmidt-Clermont et al. (1991) J. Cell Biol. 113:1081–9. This activity dramatically increases G-actin's exchange of ADP for ATP, which deactivates actin for polymerization into microfilaments and faciliatates reorganization of the cytoskeleton. Carlier (1989) Int. Rev. Cytol. 115:139–70. Profilin therefore represents an important component of the eukaryotic cell division cycle as well as, by virtue of its interaction with the actin cytoskeleton, overall cellular integrity, vesicular transport, and cell polarity.

Evidence suggests that profilin is important in the growth cycle of yeasts. Null mutation in the *Saccharomyces cerevisiae* profilin gene is lethal in many S. cerevisiae strain backgrounds. Magdolen et al. (1988) Mol. Cell Biol. 8:5108–15. In other S. cerevisiae strains, null mutations produce a strain with highly abnormal morphology and severely retarded growth rates. Haarer et al. (1990) J. Cell Biol. 110:105–14. While a role in phospholipid hydrolysis has not been shown, $PIP_2$ dependent translocation of profilin from the plasma membrane into the cytoplasm has been demonstrated. Ostrander et al. (1995) J. Biol. Chem. 46:27045–50. S. cerevisiae profilin has also been shown to interact with the RAS/adenylate cyclase pathway. Vojtek et al. (1991) Cell 66:497–505.

There is a compelling need to prevent and treat systemic fungal infections, many of which are fatal if untreated. Indeed, the 1980s and 1990s witnessed a steep rise in Candida and Aspergillus infections (Musial, C E, Cockerill III, F R, Roberts G D. (1988) *Clin Microb Rev* 1(4) :349–364; Saral R. (1991) *Reviews of Infectious Dis* 13:487–492). Similar rises in zygomycosis, cryptococcosis, histoplasmosis and fusaria infection have also been noted. The reasons for the rise in fungal infections are several, but a key factor is the growing population of immunocompromised individuals. This group includes patients with HIV disease (AIDS), older patients, patients who have undergone invasive surgery, transplant patients and burn victims.

As the population of immunosuppressed individuals increases, so do the numbers and types of fungal infections noted in these patients. Although candidiasis remains the most common fungal infection in immunosuppressed patients, aspergillosis, zygomycosis, and other infections by filamentous fungi are a major problem for an increasing number of patients (Georgiev, V. St. (1 998) Infectious Diseases in Immunocompromised Hosts, CRC Press, Boca Raton, Fla.; and Fauci, A S. (1998) Emer Infect Dis. The endemic mycoses, especially histoplasmosis and coccidiodomycosis, also constitute a risk for patients. At particular risk for such infections are those with AIDS, those having undergone bone marrow or organ transplants, those receiving chemotherapy and those who have had debilitating illness, sever injury, prolonged hospitalization, or long-term treatment with antibacterial drugs (NIAID fact sheet, 1996).

According to the CDC's National Nosocomial Surveillance System, the rate of hospital-related fungal infections nearly doubled between 1980 and 1990. In 1997, an estimated 240,000 individuals showed clinical symptoms of endemic mycoses. With the current approaches to treatment (primarily amphotericin B and the azoles) the mortality rate in patients with systemic fungal infections ranges from 30–100%, depending on the pathogen.

The severity of fungal infections increases as the immune system becomes more dysfunctional. Fungi are among the most ubiquitous pathogens seen in patients with AIDS; virtually all major fungal pathogens cause disease in HIV-positive patients The majority of untreated HIV-positive patients experience at least one episode of fungal infection and many fungal infections are AIDS-defining illnesses in HIV-infected individuals (Phillips P. (1999).

Therefore, there is a desperate need for new antifungal agents. The recent development of high-throughput screens for the isolation of such agents presents an opportunity for meeting this need. Profilin is amenable to such screening approaches and thus represents an important new target for antifungal drugs.

SUMMARY OF THE INVENTION

The present invention concerns an isolated nucleic acid molecule encoding A. fumigatus profilin. Preferably, the A. fumigatus profilin has a sequence that has greater than 70%, 80%, or 90% amino acid sequence identity to SEQ ID NO:2 as measured using a sequence comparison algorithm.

In one aspect, the invention provides an isolated nucleic acid sequence encoding A. fumigatus profilin, wherein the profilin has a sequence that has greater than 70%, 80%, or 90% amino acid sequence identity to SEQ ID NO:2 as measured using a sequence comparison algorithm. In one embodiment, the protein further specifically binds to polyclonal antibodies raised against SEQ ID NO:2.

In one embodiment, the nucleic acid encodes A. fumigatus profilin, or a fragment thereof. In another embodiment, the nucleic acid encodes SEQ ID NO:2. In another embodiment, the nucleic acid has a nucleotide sequence of SEQ ID NO:1.

In one aspect, the nucleic acid comprises a sequence which encodes an amino acid sequence which has greater than 70% sequence identity with SEQ ID NO:2, preferably greater than 80%, more preferably greater than 90%, more preferably greater than 95% or, in another embodiment, has 98 to 100% sequence identity with SEQ ID NO:2.

In one embodiment, the nucleic acid comprises a sequence which has greater than 55 or 60% sequence identity with SEQ ID NO:1, preferably greater than 70%, more preferably greater than 80%, more preferably greater than 90 or 95% or, in another embodiment, has 98 to 100% sequence identity with SEQ ID NO:1. In another embodiment provided herein, the nucleic acid hybridizes under stringent conditions to a nucleic acid having a sequence or complementary sequence of SEQ ID NO:1.

In another aspect, the invention provides an expression vector comprising a nucleic acid encoding A. fumigatus profilin, wherein the protein has a sequence that has greater than 70, 80, or 90% amino acid sequence identity to SEQ ID NO:2 as measured using a sequence comparison algorithm. The invention further provides a host cell transfected with the vector.

In another embodiment, the protein comprises an amino acid sequence of SEQ ID NO:2. In one aspect, the protein provided herein comprises an amino acid sequence which has greater than 70% sequence identity with SEQ ID NO:2, preferably greater than 80%, more preferably greater than 90%, more preferably greater than 95% or, in another embodiment, has 98 to 100% sequence identity with SEQ ID NO:2.

The invention features a substantially purified polypeptide comprising the amino acid sequence of SEQ ID NO:2 or a fragment thereof and more particularly, the ATP hydrolysis pocket or P-loop of the amino acid sequence of SEQ ID NO:2 or a fragment thereof.

Also provided are modulators of the target protein including agents for the treatment of fungal disorders. The agents and compositions provided herein can be used in variety of applications which include the formulation of sprays, powders, and other compositions. Also provided herein are methods of treating fungal disorders.

BRIEF DESCRIPTION OF THE DRAWINGS

FIG. 1 shows an embodiment of a nucleic acid sequence encoding A. fumigatus profilin (SEQ ID NO:1).

FIG. 2 shows the amino acid sequence of A. fumigatus profilin (SEQ ID NO:2).

DETAILED DESCRIPTION OF THE INVENTION

I. Definitions

Figure 3:
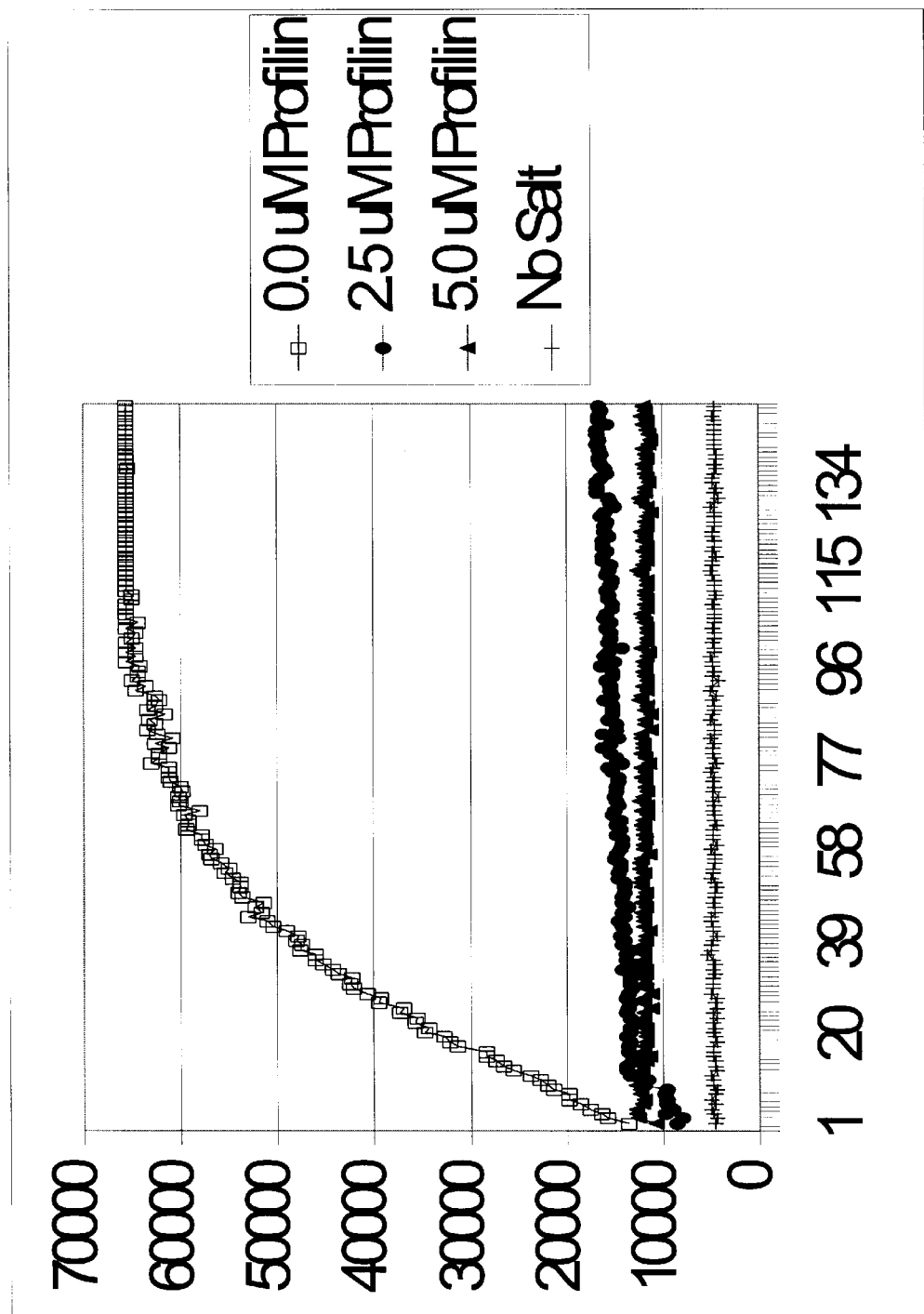
FIG. 3 shows the results of representative pyrene actin assays for A. fumigatus profilin. In the absence of profilin, pyrene actin assembles into filaments as evidenced by an increase in fluorescence over time. The addition of 5.0 uM profilin inhibits spontaneous assembly, dampening any fluorescence increase, resulting in a trace that is indistinguishable from the G-actin control (no salt). An inhibitor of profilin will result in an increase in relative fluorescence intensity. The x-axes shows cycle number (1 cycle/30 sec) and the y-axes reflect arbitrary fluorescence intensity.

"A. fumigatus profilin" refers to proteins or polypeptides present in A. fumigatus that are capable of binding actin and $PIP_2$ and has the sequence described below.

An "anti-A. fumigatus profilin" antibody is an antibody or antibody fragment that specifically binds a polypeptide encoded by the A. fumigatus profilin gene, cDNA, or a subsequence thereof.

"Biologically active" target protein refers to a target protein that has one or more of the target protein's biological activities, including, but not limited to ability to bind actin and $PIP_2$ and hydrolyze ATP.

"Biological sample" as used herein is a sample of biological tissue or fluid that contains a target protein or a fragment thereof or nucleic acid encoding a target protein or a fragment thereof. A biological sample comprises at least one cell or cell extract.

"Control region" refers to a nucleotide sequence that regulates expression of a nucleic acid or any subunit thereof, including but not limited to any promoter, silencer, enhacer, splice site, transcriptional initiation element, transcriptional termination signal, polyadenylation signal, translational control element, translational start site, translational termination site, and message stability element. Such control regions may reside 5' or 3' to the coding region or in introns interrupting the coding region.

A "comparison window" includes reference to a segment of any one of the number of contiguous position selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the global alignment algorithm of Needleman & Wunsch, J. Mol. Biol. 48:443 (1970), by the search for similarity methods of Pearson & Lipman, Proc. Natl. Acad. Sci. USA 85:2444 (1988) and Altschul et al. Nucleic Acids Res. 25(17): 3389–3402 (1997), by computerized implementations of these algorithms (GAP, BESTFIT, FASTA, and BLAST in the Wisconsin Genetics Software Package, Genetics Computer Group, 575 Science Dr., Madison, Wis., or by manual alignment and visual inspection (see, e.g., Ausubel et al., supra).

One example of a useful algorithm is PILEUP. PILEUP creates a multiple sequence alignment from a group of related sequences using progressive, pairwise alignment. It can also plot a dendrogram showing the clustering relationships used to create the alignment. PILEUP uses a simplification of the progressive alignment method of Feng & Doolittle, J Mol. Evol 35:351–360(1987). The method used is similar to the method described by Higgins & Sharp, CABIOS 5:151–153 (1989). As a general rule, PileUp can align up to 500 sequences, with any single sequence in the final alignment restricted to a maximum length of 7,000 characters.

The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment and a consensus sequence of conserved positions.

A "diagnostic" as used herein is a compound, method, system, or device that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"High stringency conditions" may be identified by those that: (1) employ low ionic strength and high temperature for washing, for example 0.015 M sodium chloride/0.015 M sodium citrate/0.1% sodium dodecyl sulfate at 50–68° C.; (2) employ during hybridization a denaturing agent such as formamide, for example, 50% (v/v) formamide with 0.1 % bovine serum albumin/0.1 % Ficoll/0.1 % polyvinylpyrrolidone/50mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay which provides for multiple candidate agents or samples to be screened simultaneously. As further described below, examples of such assays may include the use of microtiter plates which are especially convenient because a large number of assays can be carried out simultaneously, using small amounts of reagents and samples.

By "host cell" is meant a cell that contains an expression vector and supports the replication or expression of the gene contained within the expression vector. Host cells may be prokaryotic cells such as $E.\ coli$, or eukaryotic cells such as yeast, insect, amphibian, or mammalian cells such as CHO, HeLa and the like, or plant cells. Both primary cells and cultured cell lines are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of DNA duplex destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. Preferably, the percent identity exists over a region of the sequence that is at least about 25 amino acids in length, more preferably over a region that is 50 or 100 amino acids in length. This definition also refers to the complement of a test sequence, provided that the test sequence has a designated or substantial identity to a reference sequence.

Preferably, the percent identity exists over a region of the sequence that is at least about 25 nucleotides in length, more preferably over a region that is 50 or 100 nucleotides in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g,. charge or hydrophobicity) and therefore do not change the functional properties of the molecule. Where sequences differ in conservative substitutions, the percent sequence identity may be adjusted upwards to correct for the conservative nature of the substitution. Alternatively, when one includes such conservative substitutions in the comparison, a percent "similarity" can be noted, as opposed to a percent "identity". Means for making this adjustment are well known to those of skill in the art. The scoring of conservative substitutions can be calculated according to, e.g., the algorithm of Meyers & Millers, Computer Applic. Biol. Sci. 4:11–17 (1988), e.g., as implemented in the program PC/GENE (Intelligenetics, Mountain View, Calif.).

"Isogenic" refers to strains that have identical genomes but differ in a single gene, be it resident on the chromosome or a plasmid.

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated gene, the nucleic acid of interest is separated from open reading frames which flank the gene of interest and encode proteins other than the protein of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, radioisotopes such as $^{32}p$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

A "labeled nucleic acid probe or oligonucleotide" is one that is bound, either covalently, through a linker, or through ionic, van der Waals, or hydrogen bonds to a label such that the presence of the probe may be detected by detecting the presence of the label bound to the probe.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 µg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of a target protein" refer to modulatory molecules identified using in vitro and in vivo assay for target protein activity. Such assays include binding activity such as actin binding activity or binding to $PIP_2$. Samples or assays that are treated with a candidate agent at a test and control concentration. The control concentration can be zero. If there is a change in target protein activity between the two concentrations, this change indicates the identification of a modulator. A change in activity, which can be an increase or decrease, is preferably a change of at least 20% to 50%, more preferably by at least 50% to 75%, more preferably at least 75% to 100%, and more preferably 150% to 200%, and most preferably is a change of at least 2 to 10 fold compared to a control. Additionally, a change can be indicated by a change in binding specificity or substrate.

"Multi-copy plasmid" refers to a plasmid having 10 to 30 copies present in a cell.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. For example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Amino acids may be referred to herein by either their commonly known three letter symbols or by Nomenclature Commission. Nucleotides, likewise, may be referred to by their commonly accepted single-letter codes, i.e., the one-letter symbols recommended by the IUPAC-IUB.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA box element. A promoter also optionally includes distal enhancer or repressor elements which can be located as much as several thousand base pairs from the start site of transcription. A "constitutive" promoter is a promoter that is active under most environmental and developmental conditions. An "inducible" promoter is promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to *A. fumigatus* profilin with the amino acid sequence encoded in SEQ ID NO:2 can be selected to obtain only those antibodies that are specifically immunoreactive with *A. fumigatus* profilin and not with other proteins, except for polymorphic variants, orthologs, alleles, and closely related homologues of *A. fumigatus* profilin. This selection may be achieved by subtracting out antibodies that cross react with molecules, for example, such as *C. elegans* unc-104 and human Kif1A by affinity chromatography. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

"Test composition" (used interchangeably herein with "candidate agent" and "test compound" and "test agent") refers to a molecule or composition whose effect on the interaction between one or more cytoskeletal components it is desired to assay. The "test composition" can be any molecule or mixture of molecules, optionally in a carrier.

A "therapeutic" as used herein refers to a compound which is believed to be capable of modulating the target protein in vivo which can have application in both human and animal disease. Modulation of the cytoskeletal system would be desirable in a number of conditions including, but not limited to antifungal agents and anti-inflammatory agents.

"Variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCT all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each degenerate codon in a nucleic acid can be modified to yield a functionally identical molecule. Accordingly, each silent variation of a nucleic acid which encodes a polypeptide is implicit in each described sequence.

Also included within the definition of target proteins of the present invention are amino acid sequence variants of wild-type target proteins. These variants fall into one or more of three classes: substitutional, insertional or deletional variants. These variants ordinarily are prepared by site specific mutagenesis of nucleotides in the DNA encoding the target protein, using cassette or PCR mutagenesis or other techniques well known in the art, to produce DNA encoding the variant, and thereafter expressing the DNA in recombinant cell culture. Variant target protein fragments having up to about 100–150 amino acid residues may be prepared by in vitro synthesis using established techniques. Amino acid sequence variants are characterized by the predetermined nature of the variation, a feature that sets them apart from naturally occurring allelic or interspecies variation of the target protein amino acid sequence. The variants typically exhibit the same qualitative biological activity as the naturally occurring analogue, although variants can also be selected which have modified characteristics.

Amino acid substitutions are typically of single residues; insertions usually will be on the order of from about 1 to about 20 amino acids, although considerably longer insertions may be tolerated. Deletions range from about 1 to about 20 residues, although in some cases, deletions may be much longer.

Substitutions, deletions, and insertions or any combinations thereof may be used to arrive at a final derivative. Generally, these changes are done on a few amino acids to minimize the alteration of the molecule. However, larger characteristics may be tolerated in certain circumstances.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

II. The Target Protein

The present invention provides for the first time a nucleic acid encoding *A. fumigatus* profilin. This protein is a member of the profilin superfamily. More specifically, the *A. fumigatus* profilin sequence of FIG. 2 shares approximately 30–40% identity to *S. pombe* profilin; *Candida albicans* profilin; and *S. cerevisiae* profilin over 126 amino acids.

In one aspect, *A. fumigatus* profilin can be defined by having at least one or preferably more than one of the following functional and structural characteristics. Functionally, *A. fumigatus* profilin will be capable of binding actin and $PIP_2$.

The novel nucleotides sequences provided herein encode *A. fumigatus* profilin or fragments thereof. Thus, in one aspect, the nucleic acids provided herein are defined by the novel proteins provided herein. The protein provided herein comprises an amino acid sequence which has one or more of the following characteristics: greater than 70% sequence identity with SEQ ID NO:2, preferably greater than 80%, more preferably greater than 90%, more preferably greater than 95% or, in another embodiment, has 98 to 100% sequence identity with SEQ ID NO:2. As described above, when describing the nucleotide in terms of SEQ ID NO:1, the sequence identity may be slightly lower due to the degeneracy in the genetic code. Also included within the definition of the target proteins are amino acid sequence variants of wild-type target proteins.

Portions of the *A. fumigatus* profilin nucleotide sequence may be used to identify polymorphic variants, orthologs, alleles, and homologues of *A. fumigatus* profilin. This identification can be made in vitro, e.g., under stringent hybridization conditions and sequencing, or by using the sequence information in a computer system for comparison with other nucleotide sequences. Sequence comparison can be performed using any of the sequence comparison algorithms discussed below, with PILEUP as a preferred algorithm.

As will be appreciated by those in the art, the target proteins can be made in a variety of ways, including both synthesis de novo and by expressing a nucleic acid encoding the protein.

Target proteins of the present invention may also be modified in a way to form chimeric molecules comprising a fusion of a target protein with a tag polypeptide which provides an epitope to which an anti-tag antibody can selectively bind. The epitope tag is generally placed at the amino or carboxyl terminus of the target protein. Provision of the epitope tag enables the target protein to be readily detected, as well as readily purified by affinity purification. Various tag epitopes are well known in the art. Examples include poly-histidine (poly-his) or poly-histidine-glycine (poly-his-gly) tags; the influenza HA tag polypeptide and its antibody 12CA5 (see, Field et al. (1988) Mol. Cell. Biol. 8:2159); the c-myc tag and the 8F9, 3C7, 6E10, G4, B7 and 9E10 antibodies thereto (see, Evans et al., (1985) Molecular and Cellular Biology, 5:3610); and the Herpes Simplex virus glycoprotein D (gD) tag and its antibody (see, Paborsky et al., (1990) Protein Engineering, 3:547). Other tag polypeptides include the Flag-peptide (see, Hopp et al. (1988) BioTechnology 6:1204); the KT3 epitope peptide (see, Martine et al. (1992) Science, 255:192); tubulin epitope peptide (see, Skinner (1991) J. Biol. Chem. 266:15173); and the T7 gene 10 protein peptide tag (see, Lutz-Freyermuth et al. (1990) Proc. Natl. Acad. Sci. USA 87:6393.

The biological activity of any of the peptides provided herein can be routinely confirmed by the assays known in the art. In one embodiment, polymorphic variants, alleles, and orthologs, homologues of A. fumigatus profilin are confirmed by using actin or $PIP_2$ assays as known in the art.

The isolation of biologically active A. fumigatus profilin for the first time provides a means for assaying for modulators of this protein. Biologically active A. fumigatus profilin is useful for identifying modulators of A. fumigatus profilin or fragments thereof. In vivo assays and uses are provided herein as well. Also provided herein are methods of identifying candidate agents which bind to A. fumigatus profilin and portions thereof.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, agricultural and research based applications.

III. Isolation of the Gene Encoding A. fumigatus Profilin

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from mass spectroscopy, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonculeotides is by either native acrylamide gel electrophoresis or by anion-exchange HPLC as described in Pearson & Reanier, *J. Chrom.* 225:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding A. fumigatus Profilin In general, the nucleic acid sequences encoding A. *fumigatus* profilin and related nucleic acid sequence homologs are cloned from cDNA and genomic DNA libraries or isolated using amplification techniques with oligonucleotide primers. Alternatively, expression libraries can be used to clone A. *fumigatus* profilin and A. *fumigatus* profilin homologues by detected expressed homologues immunologically with antisera or purified antibodies made against A. *fumi- gatus* profilin that also recognize and selectively bind to the A. *fumigatus* profilin homologue. Finally, amplification techniques using primers can be used to amplify and isolate A. *fumigatus* profilin from DNA or RNA. Amplification techniques using degenerate primers can also be used to amplify and isolate A. *fumigatus* profilin homologues. Amplification techniques using primers can also be used to isolate a nucleic acid encoding A. *fumigatus* profilin. These primers can be used, e.g., to amplify a probe of several hundred nucleotides, which is then used to screen a library for full-length A. *fumigatus* profilin.

Appropriate primers and probes for identifying the gene encoding homologues of A. *fumigatus* profilin in other species are generated from comparisons of the sequences provided herein. As described above, antibodies can be used to identify A. *fumigatus* profilin homologues. For example, antibodies made to the conserved actin-binding domain of A. *fumigatus* profilin or to the whole protein are useful for identifying A. *fumigatus* profilin homlogues.

To make a cDNA library, one should choose a source that is rich in the mRNA of choice, e.g., A. *fumigatus* profilin. The genomic library is usually contained in, for example, a modified bacteriophage lambda or E. coli plasmid (Sambrook et al. supra). The cDNA library may be contained in such vectors as λgt10, λgt11, or lambda ZAP. The mRNA is converted into cDNA using reserve transcriptase, made double stranded, ligated into a recombinant vector, and introduced into a recombinant host for propagation, screening and cloning. Methods for making and screening cDNA libraries are well known (see, e.g., Gubler & Hoffman, Gene 25: 263–269); Sambrook et al., supra; Ausubel et al., supra).

An alternative method of isolating A. *fumigatus* profilin nucleic acid and its homologues combines the use of synthetic oligonucleotide primers and amplification of an RNA or DNA template (see U.S. Pat. Nos. 4,683,195 and 4,683, 202; PCR Protocols: A guide to Methods and Applications (Innis et al., eds. 1990)). Methods such as polymerase chain reaction and ligase chain reaction can be used to amplify nucleic acid sequences of A. *fumigatus* profilin directly from mRNA, from cDNA, from genomic libraries or cDNA libraries. Degenerate oligonucleotides can be designed to amplify A. *fumigatus* profilin homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of A. *fumigatus* profilin encoding mRNA in physiological samples, for nucleic sequencing or for other purposes. Genes amplified by the PCR reaction can be purified from agarose gels and cloned into an appropriate vector.

Gene expression of A. *fumigatus* profilin can also be analyzed by techniques known in the art, e.g., reverse transcription and amplification of mRNA, isolation of total RNA or poly A+RNA, northern blotting, dot blotting, in situ hybridization, RNase protection, quantitative PCR, and the like.

Synthetic oligonucleotides can be used to construct recombinant A. *fumigatus* profilin genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the A. *fumigatus* profilin gene. The specific subsequence is then ligated into an expression vector.

The gene for *A. fumigatus* profilin is typically cloned into intermediate vectors before transformation into prokaryotic or eukaryotic cells for replication and/or expression. The intermediate vectors are typically prokaryote vectors or shuttle vectors.

C. Expression in Prokaryotes and Eukaryotes

To obtain high level expression of a cloned gene, such as those cDNAs encoding *A. fumigatus* profilin, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the *A. fumigatus* profilin protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the *A. fumigatus* profilin encoding nucleic acid in host cells. A typical expression cassette thus contains a promoter operably linked to the nucleic acid sequence encoding *A. fumigatus* profilin and signals required for efficient polyadenylation of the transcript, ribosome binding sites, and translation termination. The nucleic acid sequence encoding *A. fumigatus* profilin may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23, and fusion expression systems such as GST and LacZ. Epitope tags can also be added to recombinant proteins to provide convenient methods of isolation, e.g., c-myc or histidine tags.

Expression vectors containing regulatory elements from eukaryotic viruses are typically used in eukaryotic expression vectors, e.g., SV40 vectors, cytomegalovirus vectors, papilloma virus vectors, and vectors derived from Epstein Bar virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 late promoter, CMV promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a *A. fumigatus* profilin encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection or transformation methods are used to produce bacterial, mammalian, yeast or insect cell lines that express large quantities of *A. fumigatus* profilin protein, which are then purified using standard techniques (see, e.g., Colley et al., *J. Biol. Chem.* 264:17619–17622 (1989); *Guide to Protein Purification*, in *Methods in Enzymology*, vol.182 (Deutscher ed., 1990)).

Transformation of eukaryotic and prokaryotic cells are performed according to standard techniques (see, e.g., Morrison, *J. Bact.*, 132:349–351 (1977); Clark-Curtiss & Curtiss, *Methods in Enzymology*, 101:347–362 (Wu et al., eds, 1983). Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing *A. fumigatus* profilin.

After the expression vector is introduced into the cells, the transfected cells are cultured under conditions favoring expression of *A. fumigatus* profilin, which is recovered from the culture using standard techniques identified below.

IV. Purification of *A. fumigatus* Profilin Protein

Either naturally occurring or recombinant *A. fumigatus* profilin can be purified for use in functional assays. In a preferred embodiment, the target proteins are purified for use in the assays to provide substantially pure samples.

The target proteins may be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography, chromatofocussing, selective precipitation with such substances as ammonium sulfate; and others (see, e.g., Scopes, Protein Purification: Principles and Practice (1982); U.S. Pat. No. 4,673,641; Ausubel et al. supra; and Sambrook et al., supra). For example, the target protein can be purified using a standard anti-target antibody column. Ultrafiltration and diafiltration techniques, in conjunction with protein concentration, are also useful. A preferred method of purification is use of Ni-NTA agarose (Qiagen) in combination with polyhistine-tagged proteins.

The expressed protein can be purified by standard chromatographic procedures to yield a purified, biochemically active protein. The activity of any of the peptides provided herein can be routinely confirmed by the assays known in the art.

A. Purification of *A. fumigatus* Profilin From Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein. Alternatively, it is possible to purify *A. fumigatus* profilin from bacteria periplasm. After *A. fumigatus* profilin is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art. Suitable purification schemes for some specific kinesins are outlined in U.S. Ser. No. 09/295,612, filed Apr. 20, 1999, hereby expressly incorporated herein in its entirety for all purposes.

B. Standard Protein Separation Techniques For Purifying *A. fumigatus* Profilin

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of *A. fumigatus* profilin can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

*A. fumigatus* profilin can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of *A. fumigatus* Profilin

In addition to the detection of *A. fumigatus* profilin genes and gene expression using nucleic acid hybridization technology, one can also use immunoassays to detect *A. fumigatus* profilin. Immunoassays can be used to qualitatively or quantitatively analyze *A. fumigatus* profilin. A general overview of the applicable technology can be found in Harlow & Lane, *Antibodies: A Laboratory Manual* (1988).

A. Antibodies to *A. fumigatus* Profilin

Methods of producing polyclonal and monoclonal antibodies that react specifically with *A. fumigatus* profilin are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of *A. fumigatus* profilin comprising immunogens may be used to produce antibodies specifically reactive with *A. fumigatus* profilin. For example, recombinant *A. fumigatus* profilin or a antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to *A. fumigatus* profilin. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-*A. fumigatus* profilin proteins or even other homologous proteins from other organisms (e.g., fungal or vertebrate profilins), using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

Once *A. fumigatus* profilin specific antibodies are available, *A. fumigatus* profilin can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio ed., 1980); and Harlow & Lane, supra.

B. Binding Assays

Antibodies can be used for treatment or to identify the presence of *A. fumigatus* profilin having the sequence identity characteristics as described herein. Additionally, antibodies can be used to identify modulators of the interaction between the antibody and *A. fumigatus* profilin as further described below. While the following discussion is directed toward the use of antibodies in the use of binding assays, it is understood that the same general assay formats such as those described for "non-competitive" or "competitive" assays can be used with any compound which binds to *A. fumigatus* profilin such as microtubules or the compounds described in Ser. No. 60/070,772.

In a preferred embodiment, *A. fumigatus* profilin is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37*: Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the *A. fumigatus* profilin or antigenic subsequence thereof). The antibody (e.g., anti-*A. fumigatus* profilin) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled *A. fumigatus* profilin polypeptide or a labeled anti-*A. fumigatus* profilin antibody. Alternatively, the labeling agent may be a third moiety, such a secondary antibody, that specifically binds to the antibody/*A. fumigatus* profilin complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 4° C. to 40° C.

Non-Competitive Assay Formats

Immunoassays for detecting *A. fumigatus* profilin in samples may be either competitive or noncompetitive. Noncompetitive immunoassays are assays in which the amount of antigen is directly measured. In one preferred "sandwich" assay, for example, the anti-*A. fumigatus* profilin antibodies can be bound directly to a said substrate on which they are immobilized. These immobilized antibodies then capture *A. fumigatus* profilin present in the test sample. *A. fumigatus* profilin is thus immobilized is then bound by a labeling agent, such as a second *A. fumigatus* profilin antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of *A. fumigatus* profilin present in the sample is measured indirectly by measuring the amount of a known, added (exogenous) *A. fumigatus* profilin displaced (competed away) from an anti-*A. fumigatus* profilin antibody by the unknown *A. fumigatus* profilin present in a sample. In one competitive assay, a known amount of *A. fumigatus* profilin is added to a sample and the sample is then contacted with an antibody that specifically binds to *A. fumigatus* profilin. The amount of exogenous *A. fumigatus* profilin bound to the antibody is inversely proportional to the concentration of *A. fumigatus* profilin present in the sample. In a particularly preferred embodiment, the antibody is immobilized on a solid substrate. The amount of *A. fumigatus* profilin bound to the antibody may be determined either by measuring the amount of *A. fumigatus* profilin present in a *A. fumigatus* profilin/antibody complex, or alternatively by measuring the amount of remaining uncomplexed protein. The amount of *A. fumigatus* profilin may be detected by providing a labeled *A. fumigatus* profilin molecule.

Cross-reactivity Determinations

Immunoassays in the competitive binding format can also be used for crossreactivity determinations. For example, a protein at least partially encoded by SEQ ID NO:2 can be immobilized to a solid support. Proteins (e.g., other fungal or vertebrate profilins) are added to the assay that compete for binding of the antisera to the immobilized antigen. The ability of the added proteins to compete for binding of the antisera to the immobilized protein is compared to the ability of *A. fumigatus* profilin encoded by SEQ ID NO:2 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., *A. fumigatus* profilin of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a *A. fumigatus* profilin immunogen.

Other Assay Formats

Western blot (immunoblot) analysis is used to detect and quantify the presence of *A. fumigatus* profilin in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind *A. fumigatus* profilin. The anti-*A. fumigatus* profilin antibodies specifically bind to the *A. fumigatus* profilin on the solid support. These antibodies may be directly labeled or alternatively may be subsequently detected using labeled antibodies (e.g., labeled sheep anti-mouse antibodies) that specifically bind to the anti-*A. fumigatus* profilin antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or *chemical means*. Useful labels in the present invention include magnetic beads (e.g., DYNABEADS™), fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), colorimetric labels such as colloidal gold or colored glass or plastic beads (e.g., polystyrene, polypropylene, latex, etc.) or other labels that can be detected by mass spectroscopy, NMR spectroscopy, or other analytical means known in the art.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize *A. fumigatus* profilin, or secondary antibodies that recognize anti-*A. fumigatus* profilin.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of the Target Protein

The present invention provides methods to identify candidate agents that bind to a target protein or act as a modulator of the binding characteristics or biological activity of a target protein. In one embodiment, the method is performed in plurality simultaneously. For example, the method can be performed at the same time on multiple assay mixtures in a multi-well screening plate. Thus, in one aspect, the invention provides a high throughput screening system.

More specifically, the methods of the present invention can be used to identify inhibitors of profilin that have antifungal activity and that therefore provide the starting point for maturing a candidate compound for clinical development. These methods can be used to identify inhibitors that show biochemical inhibition of bacterially expressed *Aspergillus fumigatus* and *Candida albicans* profilin in vitro and counterscreened against human profilin. In a particularly preferred embodiment, the method also comprises the further step of measuring the toxicity of the compounds of interest on mammalian cells.

Genes encoding *A. fumigatus* profilin were cloned by amplifying fragments of *Aspergillus nidulans* ESTs, then screening an *Aspergillus fumigatus* cDNA library at low stringency. The protein was expressed in *E. coli*, and was purified to homogeneity. Using this method, tens to hundreds of milligrams of purified protein per liter of culture, can be obtained. The protein exhibited the biochemical activities previously demonstrated for homologs isolated from other organisms. *Candida albicans* proteins were obtained by cloning the respective genes using publically available sequence information, designing appropriate primers, performing PCR, and expressing these cloned genes as described above. *Candida albicans* profilin was purified to homogeneity as described for *A. fumigatus* profilin. See, e.g., PCT Publication WO 97/31104, which is incorporated herein by reference for all purposes.

Assays for the interaction of *A. fumigatus* and any other profilin with actin in 384-well plates using a fluorescence as the detection means have been developed. The assays employ pyrene-labeled actin (Pollard (1984) J Cell Biol 99:769–777). When pyrene actin assembles, the quantum yield of fluorescence increases 25-fold (FIG. 3). This very robust signal can be exploited to an assay for modulators of profilin. Chicken skeletal actin was used because it can be purified in quantities needed for high throughput screening; it is 90% identical in amino acid sequence to fungal actin, and it can assemble into copolymers with fungal actin. Pyrene-labeled skeletal actin has been prepared and characterized as to its polymerization properties as well as for its interaction with fungal profilin.

The kinetics of actin assembly in the absence and presence of profilin can be monitored. Actin assembly proceeds in three phases. There is a lag phase during which time seeds form from three actin monomers. This is followed by an elongation phase during which filaments are extended from seeds. Finally, at steady state, the polymer concentration is constant, although filaments treadmill. Although actin bound to profilin can elongate the barbed ends of pre-existing actin filaments, profilin very potently inhibits the nucleation of filaments de novo (Pollard et al. (1984) Biochem. 23:6631–6641.). FIG. 3 shows inhibition of pyrene-actin nucleation by *A. fumigatus* profilin in a 384-well plate assay. An inhibitor of the interaction of profilin with actin should overcome this inhibition of actin nucleation and cause a pronounced increase in pyrene fluorescence, ideally to levels approaching that seen in the absence of profilin.

Accordingly, the present invention provides for a high throughput method for the identification of small molecules that inhibit or modulate profilin interactions with actin. Several biochemical assays (many of which assess key in vivo functions of the proteins) exist for profilin (Kreis, T and Vale, R (eds) (1999) *Guidebook to the Cytoskeletal and Motor Proteins*. Oxford University Press, Oxford). For example, etheno-ATP fluorescence can be used to screen for compounds that inhibit profilin's enhancement of actin nucleotide exchange; genetic evidence suggests that this activity is critical in vivo (Wolven et al., 2000).

C. Candidate Agents

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

VII. Applications

Fungal infections which can be inhibited or treated with compositions provided herein include but are not limited to: Candidiasis including but not limited to onchomycosis, chronic mucocutaneous candidiasis, oral candidiasis, epiglottistis, esophagitis, gastrointestinal infections, genitourinary infections, for example, caused by any Candida species, including but not limited to *Candida albicans, Candida tropicalis, Candida (Torulopsis) glabrata, Candida parapsilosis, Candida lusitaneae, Candida rugosa* and *Candida pseudotropicalis*; Aspergillosis including but not limited to granulocytopenia caused for example, by, Aspergillus spp. including but not limited to *A. fumigatus, Aspergillus flavus, Aspergillus niger* and *Aspergillus terreus*; Zygomycosis, including but not limited to pulmonary, sinus and rhinocerebral infections caused by, for example, zygomycetes such as Mucor. Rhizopus spp., Absidia, Rhizomucor, Cunningamella, Saksenaea, Basidobolus and Conidobolus; Cryptococcosis, including but not limited to infections of the central nervous system—meningitis and infections of the respiratory tract caused by, for example, *Cryptococcus neoformans*; Trichosporonosis caused by, for example, *Trichosporon beigelii*; Pseudallescheriasis caused by, for example, *Pseudallescheria boydii*; Fusarium infection caused by, for example, Fusarium such as *Fusarium solani, Fusarium moniliforme* and *Fusarium proliferatum*; and other infections such as those caused by, for example, Penicillium spp. (generalized subcutaneous abscesses), Drechslera, Bipolaris, Exserohilum spp., *Paecilomyces lilacinum, Exophila jeanselmei* (cutaneous nodules), *Malassezia furfur* (folliculitis), Alternaria (cutaneous nodular lesions), *Aureobasidium pullulans* (splenic and disseminated infection), Rhodotorula spp. (disseminated infection), Chaetomium spp. (empyema), *Torulopsis candida* (fungemia), Curvularia spp. (nasopharnygeal infection), Cunninghamella spp. (pneumonia), *H. Capsulatum, B. dermatitidis, Coccidioides immitis, Sporothrix schenckii* and *Paracoccidioides brasiliensis, Geotrichum candidum* (disseminated infection).

Treating "fungal infections" as used herein refers to the treatment of conditions resulting from fungal infections. Therefore, one may treat, for example, pneumonia, nasopharnygeal infections, disseminated infections and other conditions listed above and known in the art by using the compositions provided herein. In preferred embodiments, treatments and sanitization of areas with the compositions provided herein are provided to immunocompromised patients or areas where there are such patients. Wherein it is desired to identify the particular fungi resulting in the infection, techniques known in the art may be used, see, for example, Musial et al., Clin. Microbiol. Rev., American Society for Microbiology, 349–64 (1998), incorporated herein by reference.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis or in which cell morphology (e.g., filamentous hyphal growth, etc.) can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Candidate agents having the desired pharmacological activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1–100 wt. %. The agents maybe administered alone or in combination with other treatments, i.e., radiation, or other chemotherapeutic agents.

In a preferred embodiment, the pharmaceutical compositions are in a water soluble form, such as pharmaceutically acceptable salts, which is meant to include both acid and base addition salts.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the candidate agents of the present invention can be done in a variety of ways as discussed above, including, but not limited to, orally, subcutaneously, intravenously, intranasally, transdermally, intraperitoneally, intramuscularly, intrapulmonary, intrathecally, vaginally, rectally, or intraocularly. In some instances, for example, in the treatment of wounds and inflammation, the candidate agents may be directly applied as a solution or spray.

One of skill in the art will readily appreciate that the methods described herein also can be used for diagnostic applications. A diagnostic as used herein is a compound or method that assists in the identification and characterization of a health or disease state in humans or other animals. More specifically, antibodies which specifically bind *A. fumigatus* profilin may be used for the diagnosis of disorders characterized by expression of *A. fumigatus* profilin or in assays to monitor patients being treated with *A. fumigatus* profilin, or agonists, antagonists, or inhibitors of *A. fumigatus* profilin. Diagnostic assays include methods which utilize the antibody and a label to detect *A. fumigatus* profilin in human body fluids or in extracts of cells or tissues. The antibodies may be used with or without modification, and may be labeled by covalent or non-covalent attachment of a reporter molecules. A wide variety of reporter molecules are known in the art and may be used.

A variety of protocols for measuring *A. fumigatus* profilin, including ELISAs, RIAs, and FACS, are known in the art and provide a basis for diagnosing altered or abnormal levels of *A. fumigatus* profilin expression. Normal or standard values for *A. fumigatus* profilin expression are established by combining body fluids or cell extracts taken from normal mammalian subjects, preferably human, with antibody to *A. fumigatus* profilin under conditions suitable for complex formation. The amount of standard complex formation may be quantitated by various methods, preferably by photometric means. Quantities of *A. fumigatus* profilin expressed in subject, control, and disease samples from biopsied tissues can be compared with the standard values. Deviation between standard and subject values establishes the parameters for diagnosing disease.

In another embodiment of the invention, the polynucleotides encoding *A. fumigatus* profilin may be used for diagnostic purposes. The polynucleotides which may be used include oligonucleotide sequences, complementary RNA and DNA molecules, and PNAs. The polynucleotides may be used to detect and quantitate gene expression in biopsied tissues in which *A. fumigatus* profilin may be correlated with disease. The diagnostic assay may be used to determine absence, presence, and excess expression of *A. fumigatus* profilin, and to monitor regulation of *A. fumigatus* profilin levels during therapeutic intervention.

In one aspect, hybridization with PCR probes which are capable of detecting polynucleotide sequences, including genomic sequences encoding *A. fumigatus* profilin or closely related molecules may be used. The specificity of the probe, whether it's made from a highly specific region or from a less specific region, and the stringency of the hybridization or amplification (maximal, high, intermediate, or low) will determine whether the probe identifies only naturally occurring sequences encoding *A. fumigatus* profilin, allelic variants, or related sequences.

Probes may also be used for the detection of related sequences, and should preferably have at least 50% sequence identity to any of the *A. fumigatus* profilin encoding sequences. The hybridization probes of the subject invention may be DNA or RNA and may be derived from the sequence of SEQ ID NO:1 or from genomic sequences including promoters, enhancers, and introns of the *A. fumigatus* profilin gene.

Means for producing specific hybridization probes for DNAs encoding *A. fumigatus* profilin include the cloning of polynucleotide sequences encoding *A. fumigatus* profilin or derivatives thereof into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems and the like.

In a particular aspect, the nucleotide sequences encoding *A. fumigatus* profilin may be useful in assays that detect the presence of associated disorders. The nucleotide sequences encoding *A. fumigatus* profilin may be labeled by standard methods and added to a fluid or tissue sample from a patient under conditions suitable for the formation of hybridization complexes. After a suitable incubation period, the sample is washed and the signal is quantitated and compared with a standard value. If the amount of signal is significantly altered in comparison to a control sample then the presence of altered levels of nucleotide sequences encoding *A. fumigatus* profilin in the sample indicates the presence of the associated disorder. Such assays may also be used to evaluate the efficacy of a particular therapeutic treatment regimen in animal studies, in clinical trials, or to monitor the treatment of an individual patient.

Additional diagnostic uses for oligonucleotides designed from the sequences encoding *A. fumigatus* profilin may involve the use of PCR. These oligomers may be chemically synthesized, generated enzymatically, or produced in vitro based on SEQ ID NO:1. Oligomers will preferably contain a fragment of a polynucleotide encoding *A. fumigatus* profilin, or a fragment of a polynucleotide complementary to the polynucleotide encoding *A. fumigatus* profilin, and will be employed under optimized conditions for identification of a specific gene or condition. Oligomers may also be employed under less stringent conditions for detection or quantitation of closely related DNA or RNA sequences. Quantitative PCR as practiced by those of skill in the art can be used to detect relative levels of *A. fumigatus* mRNA in a test sample.

Methods which may be used to quantitate the expression of *A. fumigatus* profilin include radiolabeling or biotinylating nucleotides, coamplification of a control nucleic acid, and interpolating results from standard curves. The speed of quantitation of multiple samples may be accelerated by running the assay in an ELISA format where the oligomer of interest is presented in various dilutions and a spectrophotometer or calorimetric response gives rapid quantitation.

One of skill in the art will readily appreciate that the methods described herein also can be used for diagnostic applications. A diagnostic as used herein is a compound or method that assists in the identification and characterization of a health or disease state in humans or other animals.

The present invention also provides for kits for screening for modulators of the target protein. Such kits can be prepared from readily available materials and reagents. For example, such kits can comprise any one or more of the following materials: biologically active target protein, reaction tubes, and instructions for testing activity of the target protein. Preferably, the kit contains biologically active target protein. A wide variety of kits and components can be prepared according to the present invention, depending upon the intended user of the kit and the particular needs of the user. For example, the kit can be tailored for actin binding assays.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

1. Preparation on Actin Acetone Powder From Chicken Muscle

Mince 2 kg of fresh, boneless, skinless chicken breast in a pre-chilled meat grinder (coarse grind). Extract with moderate stirring in 4 L of 0.1 M KCL, 0.15 M Potassium Phosphate, pH. 6.5 for 10 mins at 4° C. Centrifuge at 5,000 rpm for 10 mins at 4° C. Extract the pellets with strirring in 4 L of 0.05 M $NaHCO_3$ for exactly 5 minutes at 4° C. Repeat. Extract the pellets once with stirring in 4 L of 1 mM EDTA, pH 7.0 at 4° C. Extract the pellets once with stirring in 4 L of nano-pure $dH_2O$ for 10 mins. at 4° C. Carefully collect the pellets (part solid and gelatinous) into an 8 L beaker. Extract 5 times with stirring in 4 L of pre-chilled acetone for 10 mins. at room temperature in a fume hood. For each extraction, decant the top layer of acetone, then pass the remaining protein precipitate through one-layer of cheesecloth. Gently squeeze the residual acetone without adding excessive pressure. Layer the protein powder (residue) unto a glass pyrex dish lined with cheesecloth. Cover with another layer of cheesecloth and dry in the fume hood overnite. Store the residue in a wide mouth plastic bottle at −20° C. overnite. From 4 kg of chicken breast meat, a total of 450 g of actin acetone powder was generated.

2. "Clean" Chicken Breast Actin

Extract chicken breast acetone powder (as prepared above) in Buffer A: Use 200 ml of cold buffer A per 10 g of powder. Collect the extract by passing and squeezing the mixture through several layers of pre-sterilized cheesecloth. Re-extract the residue in the same volume of buffer A. Combine the extracts. Discard the extracted powder. Spin in JLA10 rotor(s) at 10 K rpm for 1 hr at 4° C. Collect the supernatant through 2 layers of pre-sterilized cheesecloth. Add $Na_2ATP$ to 0.2 mM and $MgCL_2$ to 50 mM. Stir on stir plate for 60 mins at 4° C. to allow actin to polymerize and form para-crystals. Note: $Na_2ATP$ is at 100 mM stock (pH 8,0)and $MgCL_2$ at 1M (pH 8.0) Slowly add solid KCL to 0.6 M (45 g per L of buffer) and stir at 4° C. for 30 mins. Spin in JLA 10 rotor(s) at 10K rpm for 1 hr at 4° C. Discard the supernatant and quickly rinse the surface of the pellets with cold buffer A. Dischard the wash. Add a small amount of cold buffer A (about 25–30 ml) to each bottle to soften the pellets. Resuspend vigorously by shaking the capped bottles by hand. Combine the pellets into a clean bottle and adjust the volume with buffer A so that 3ml of buffer A is used per gram of original powder. Homogenize by using a large douncer (pestle B) on ice. Dialyze against buffer A with 4 changes over a 48 hour period at 4° C. with stirring. Collect the dialyzed Actin and spin at 40K rpm using a 45Ti rotor at 4° C. for 1 hr. Collect the supernatant (G-Actin). To polymerize G-actin for storage add KCL to 50 mM (from 3 M stock), $MgCl_2$ to 1 mM and $NaN_3$ to 0.02% (from 10% stock).

Buffer A
  2 mM Tris
  0.2 mM $CaCl_2$
  0.005% $NaN_3$
  0. 5 mM B-mercaptoethanol (36 ul per liter)
  0.2 mM $Na_2ATP$
  pH 8.0 when making 1×solution

3. Pyrene-Actin

Start with "Clean" actin as prepared above. Adjust the concentration of clean actin to 40–·.·uM with G- buffer. Dialyze several times against G-buffer with No DTT or 2-mercaptoethanol over night or longer. After dialysis, transfer actin into a foil-wrapped tube or bottle. In rapid succession, add the following into the bottle:

1. $MgCl_2$ to 2 mM (use 1 M stock)
2. *Pyrene to 45 uM with gentle mixing (use 60×stock; see below)
3. KCL to 0.1 M (use 3 M stock)

Incubate in the dark for 90 minutes at 20° C. with gentle shaking or stirring. Pellet the F-Actin (polymerized) in a TLA100.3 rotor. At 90 K rpm for 15 mins. Combine the pellets and resuspend in G-buffer to a final concentration of about 60 uM. Dialyze against several liters of G-buffer with DTT or 2-mercaptoethanol over night or for a few days at 4° C. in the dark. Do a clearing spin to remove the precipitated pyrene and denatured actin at 90 K for 15 mins or 45 K for 1 hour. Tranfer the G-actin into a sterile bottle on ice and in the dark. Drop freeze in liquid nitrogen and store pellets in a dark (foiled) bottle at −80° C.

Measure pyrene concentration at 339 nM (E=28,100/cm/M), actin concentration after pyrene labeling ($OD_{290-0.33}$× $OD_{339}$)/24.9

*Pyrene Iodoacetamide: Dissolve pyrene in anhydrous DMSO to 1 mg/ml (2.6 mM). This becomes a 60×dilution which you will use to get a final concentration of 45 uM in step. No. 5. (Molecular probes P-29, N-1 (pyrene) iodoacetamide)

Optimized profilin Assays: Inhibition of Actin Assembly

Assay Conditions (for Plate Reader Experiments, 50 ul per well)

Thaw Actin, Pyrene-Actin and Profilin pellets on ice or at room temp. (approx. 500 ul per sample), then on ice at all times. Ultra-centrifuge (Beckman) Actin and Pyrene-actin at 100,000 rpm for 30 min to 1 hour at 4° C. Remove 75% of the top layer and transfer to a sterile tube. Take readings at $OD_{290}$. Calculate concentrations in uM using $OD_{290}$ of 0.6=25 uM (or 1 mg/ml). Actin concentrations are kept constant at 6 uM and Pyrene-actin at 2 uM. 25 ul of salts will be added last. Vary profilin concentrations from 0 uM to 5.0 or 7.5 uM.

Add 25 ul of sample into each well. Add 25 ul of 2X initiation salts to each well. Take Pyrene-Kinetic readings (Fluorostar setting) at 150 cycles, 360 to 407 nM.

G Buffer
  5 mM Tris-Cl, pH 8.0
  0.2 mM ATP
  0.1 mM CaCl2
  0.5 mM DTT

10×Initiation Salts
  500 mM KCL
  10 mM MgCl2
  100 mM Tris-Cl, pH 8.0

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. An isolated *Aspergillus fumigatus* profilin protein, wherein the protein 1) comprises a sequence having greater than 95% amino acid sequence identity to SEQ ID NO:2 as measured using a sequence comparison algorithm, and 2) binds monomeric actin.

2. An isolated protein of claim 1, wherein the protein has a sequence that has greater than 98% amino acid sequence identity to SEQ ID NO:2 as measured using a sequence comparison algorithm.

3. The isolated protein of claim 1, wherein the protein specifically binds to polyclonal antibodies generated against a protein comprising SEQ ID NO:2.

4. An isolated protein wherein the protein comprises the amino acid sequence of SEQ ID NO:2.

* * * * *

SEQUENCE LISTING

<160> NUMBER OF SEQ ID NOS: 2

<210> SEQ ID NO 1
<211> LENGTH: 396
<212> TYPE: DNA
<213> ORGANISM: Aspergillus fumigatus

<400> SEQUENCE: 1
atgggtcagc actcggcagt ttggcaagga tatgttgatt ccagtttgat gggctccggc      60

```
cagtttgaca aggccgccat tctgagctac gacttctccg acgtcgaggc ccagtcccct    120
actttccaga tctcgaagga ggaaattgcc gggctgaagg ctgctttcga caagcctggc    180
agtgctttcg aaaccggttt cgtggtcgga ggagacaagt tcgtcgccat caaggctgat    240
gatcgcagtc tctacggcaa gaagggcaaa gagggtatcg tcgtcgtcaa ggccgtctct    300
tgcgtcatgg tggcccatca tggcgaggcc gttcagacca ccaacgctgc aaccgttgtc    360
gagaacctcg tcgactacat caacaacccc cggtag                              396
```

<210> SEQ ID NO 2
<211> LENGTH: 131
<212> TYPE: PRT
<213> ORGANISM: Aspergillus fumigatus

<400> SEQUENCE: 2

```
Met Gly Gln His Ser Ala Val Trp Gln Gly Tyr Val Asp Ser Ser Leu
1               5                   10                  15

Met Gly Ser Gly Gln Phe Asp Lys Ala Ala Ile Leu Ser Tyr Asp Phe
            20                  25                  30

Ser Asp Val Glu Ala Gln Ser Pro Thr Phe Gln Ile Ser Lys Glu Glu
        35                  40                  45

Ile Ala Gly Leu Lys Ala Ala Phe Asp Lys Pro Gly Ser Ala Phe Glu
    50                  55                  60

Thr Gly Phe Val Val Gly Gly Asp Lys Phe Val Ala Ile Lys Ala Asp
65                  70                  75                  80

Asp Arg Ser Leu Tyr Gly Lys Lys Gly Lys Glu Gly Ile Val Val Val
                85                  90                  95

Lys Ala Val Ser Cys Val Met Val Ala His His Gly Glu Ala Val Gln
            100                 105                 110

Thr Thr Asn Ala Ala Thr Val Val Glu Asn Leu Val Asp Tyr Ile Asn
        115                 120                 125

Asn Pro Arg
    130
```